United States Patent
Yao (10) Patent No.: US 9,554,776 B2
(45) Date of Patent: *Jan. 31, 2017

(54) METHOD FOR ADJUSTING ROI AND 3D/4D IMAGING APPARATUS USING THE SAME

(71) Applicant: Shenzhen Mindray Bio-Medical Electronics Co., Ltd., Shenzhen (CN)

(72) Inventor: Bin Yao, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 319 days.

This patent is subject to a terminal disclaimer.

(21) Appl. No.: 14/271,288

(22) Filed: May 6, 2014

(65) Prior Publication Data

US 2014/0253690 A1 Sep. 11, 2014

Related U.S. Application Data

(63) Continuation of application No. 13/163,458, filed on Jun. 17, 2011, now Pat. No. 8,723,925.

(30) Foreign Application Priority Data

Jun. 21, 2010 (CN) .......................... 2010 1 0204379

(51) Int. Cl.
*A61B 8/00* (2006.01)
*A61B 8/08* (2006.01)

(52) U.S. Cl.
CPC ............... *A61B 8/469* (2013.01); *A61B 8/466* (2013.01); *A61B 8/483* (2013.01); *A61B 8/486* (2013.01); *A61B 8/54* (2013.01); *A61B 8/4245* (2013.01)

(58) Field of Classification Search
CPC ........ A61B 8/4245; A61B 8/466; A61B 8/469
See application file for complete search history.

(56) References Cited

U.S. PATENT DOCUMENTS

| | | | | |
|---|---|---|---|---|
| 5,396,418 A | * | 3/1995 | Heuscher | 378/15 |
| 8,723,925 B2 | | 5/2014 | Yao | |
| 2006/0184031 A1 | * | 8/2006 | Ichioka et al. | 600/447 |
| 2006/0239540 A1 | * | 10/2006 | Serra et al. | 382/154 |
| 2006/0241432 A1 | | 10/2006 | Herline et al. | |

(Continued)

FOREIGN PATENT DOCUMENTS

| CN | 1810212 A | 8/2006 |
|---|---|---|
| CN | 101164499 A | 4/2008 |

(Continued)

OTHER PUBLICATIONS

Office Action mailed Jun. 20, 2013 for U.S. Appl. No. 13/163,458, filed Jun. 17, 2011.

(Continued)

*Primary Examiner* — Dave Czekaj
*Assistant Examiner* — Md Haque
(74) *Attorney, Agent, or Firm* — Kory D. Christensen; Stoel Rives LLP (57) ABSTRACT

A three-dimensional/four-dimensional (3D/4D) imaging apparatus and a region of interest (ROI) adjustment method and device are provided. An ROI is adjusted through an E image in a 3D/4D imaging mode, in which the E image is refreshed in real time when the ROI is adjusted and has a scan line range larger than that of the ROI.

12 Claims, 9 Drawing Sheets

(56) References Cited

U.S. PATENT DOCUMENTS

2007/0239009 A1* 10/2007 Kawashima et al. ......... 600/437
2008/0287803 A1 11/2008 Li et al.

FOREIGN PATENT DOCUMENTS

| CN | 101190124 A | 6/2008 |
| CN | 101513350 A | 8/2009 |
| WO | 2004070350 A2 | 8/2004 |

OTHER PUBLICATIONS

Office Action mailed Oct. 21, 2013 for U.S. Appl. No. 13/163,458, filed Jun. 17, 2011.
Office Action mailed Mar. 12, 2014 for U.S. Appl. No. 13/163,458, filed Jun. 17, 2011.

* cited by examiner

METHOD FOR ADJUSTING ROI AND 3D/4D IMAGING APPARATUS USING THE SAME

CROSS-REFERENCE TO RELATED APPLICATIONS

This application claims the benefit of Chinese Patent Application No. 201010204379.X, filed on Jun. 21, 2010, which is incorporated herein by reference.

TECHNICAL FIELD

This disclosure relates generally to a three-dimensional/four-dimensional (3D/4D) imaging apparatus, and more particularly, to methods and apparatuses for adjusting the region of interest (ROI) in 3D/4D imaging.

SUMMARY

Methods and apparatuses for adjusting the ROI in 3D/4D imaging are disclosed. In one configuration, an apparatus adjusts the ROI through an E image in a 3D/4D imaging mode, where the E image has a scan line range larger than that of the ROI.

BRIEF DESCRIPTION OF THE DRAWINGS

FIG. 3-a is a schematic view of a scan mode in imaging;

FIG. 3-b is a schematic view of a scan mode in ROI adjustment;

FIG. 4-a is a schematic view of a scan mode;

FIG. 4-b is a schematic view illustrating comparison between scanning of an E image frame and scanning of an ROI frame;

FIG. 6-a is a schematic view of a scan mode in imaging; and

FIG. 6-b is a schematic view of a scan mode in ROI adjustment.

DETAILED DESCRIPTION

Currently, medical imaging (e.g., 3D/4D ultrasonic imaging) generally includes two basic modes. One is a preview mode, in which a common B image is displayed, and a user defines a region of interest (ROI) in a region of the B image. The other is a 3D/4D imaging mode, in which 3D or 4D imaging is performed on the ROI, so as to display a section image or a 3D/4D image, or display a section image and a 3D/4D image at the same time.

Typically, 3D/4D imaging is implemented in the following manner. In the preview mode, a volume probe for collecting data (a probe capable of directly collecting 3D volume data, so that a real-time 3D image of a scanned part can be seen) does not swing and stops at a central position (a position of a 0-degree angle), and the front end of the imaging apparatus scans as for a common B image. In the preview mode, an ROI may be adjusted. The adjustment of the ROI is mainly to select a scan line range for imaging. A begin line number of the scan line range may be designated BeginLineID_ROI, and an end line number of the scan line range may be designated EndLineID_ROI. Then, when entering the 3D/4D imaging mode, the probe swings back and forth at a certain speed according to a swing angle and the ROI selected by a user.

Figure 1:
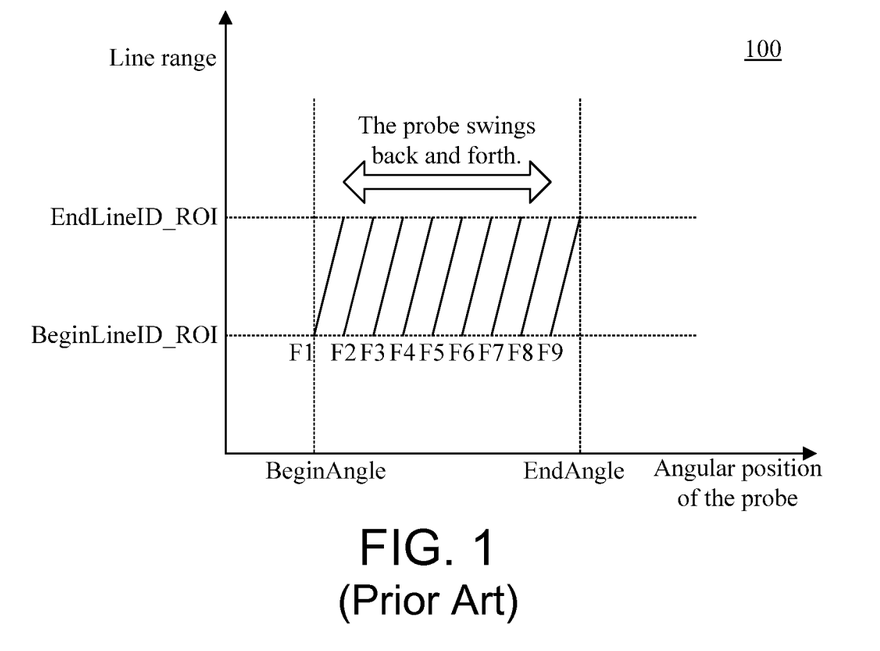
FIG. 1 is a schematic view of a conventional scan mode for 3D/4D imaging.

An example of this scan mode 100 is as shown in FIG. 1. As illustrated, the horizontal axis represents an angular position of the probe while swinging, and the vertical axis represents the scan line range. The probe swings back and forth in a swing angle range [BeginAngle, EndAngle]. F1, F2, . . . , and F9 are frame scan trajectories of the probe swinging from one side to the other side. A total of 9 frames of images (referred to as volume data) are collected. A scan line range of each frame of image is a scan line range [BeginLineID_ROI, EndLineID_ROI] of the ROI selected by the user. A depth of each frame of image is a depth of the ROI selected by the user. If a scan plane formed by a scan line range and a scan angle is regarded as being on an X-Y plane of an XYZ coordinate system, the scan depth is equivalent to a scan range along the Z axis, which is not shown in FIG. 1. Due to the swing of the probe, each frame of image is actually scanned along a trajectory of an oblique line. Each set of volume data may generate one frame of a 3D image. A series of 3D images are generated with the continuous back-and-forth swing of the probe, so as to form a 4D image sequence.

Conventionally, the ROI adjustment must be performed in the preview mode. That is to say, if the process is in the 3D/4D imaging mode, it needs to stop 3D/4D imaging and return to the preview mode to adjust the ROI. The process may be as follows:

Step 1: enter the preview mode;
Step 2: adjust the ROI;
Step 3: enter the 3D/4D imaging mode; and
Step 4: if the ROI needs to be re-adjusted, stop the 3D/4D imaging and return to Step 1.

It can be observed that the ROI adjustment process in conventional systems is complicated.

One aspect of this disclosure is to combine ROI adjustment and 3D/4D imaging, so that a user can adjust an ROI during 3D/4D imaging without frequent switching between a preview mode and a 3D/4D imaging mode, that is, the user can directly adjust the ROI in the 3D/4D imaging mode.

In a common 3D/4D imaging mode, the types of images that may be obtained from the imaging process and displayed on a screen include a section image and a 3D/4D image. The user may selectively display either of the two types of images or display both of them at the same time according to a certain layout. In certain embodiments of this disclosure, an additional E image is provided for ROI adjustment, and the user may selectively display one of a section image, a 3D/4D image, and an E image on a display screen in the 3D/4D imaging mode, or display any two of them at the same time according to a certain layout, or display all of them. The E image is obtained during the 3D/4D imaging process. In one embodiment, the E image is obtained in the 3D/4D imaging mode together with obtaining the section images or the 3D/4D images. For the 3D/4D imaging mode, the types of images that the user is interested in are mainly section images and/or 3D/4D images. Therefore, the E image that may be displayed alone on the display screen may exist in a transient state for ROI adjustment, i.e., for the convenience of ROI adjustment, the E image may be displayed alone on the full screen at a certain time, so as to be observed in a better way for adjusting the ROI. After the adjustment is completed, the E image may be hidden to display either or both of the section image and the 3D/4D image alone; or the E image may be reduced from the full screen to a part of the screen, and be displayed at the same time with either or both of the section image and the 3D/4D image. The E image may be basically a simplification of a B image in terms of data size, and generally has smaller scan line range and scan depth than those of the B image (the scan line range and the scan depth of the E image may be equal to those of the B image), so that the E image may contain less image data, which is easy to collect and display in the 3D/4D imaging mode. The E image has a larger scan line range than that of an ROI frame, and may be refreshed in real time when the ROI is adjusted. In addition, the scan depth of the E image may be larger than or equal to that of the ROI frame.

As used herein, an image frame for ROI adjustment in a preview mode is referred to as a "full frame" (a frame of a B image), and a frame collected according to a defined ROI is referred to as an "ROI frame." For example, F1 to F9 in FIG. 1 are ROI frames. Generally speaking, an image range of the ROI frame is smaller than that of the full frame, and a scan range of the full frame includes that of the ROI frame. In various embodiments, a scan range of an E image frame may be larger than that of the ROI frame, and be smaller than or equal to that of the full frame.

In a method for adjusting the ROI in 3D/4D, the ROI is adjusted through the E image in the 3D/4D imaging mode, so that the ROI can be adjusted in the 3D/4D imaging mode without switching to the preview mode. Thus, the ROI adjustment is simple and convenient.

Figure 2:
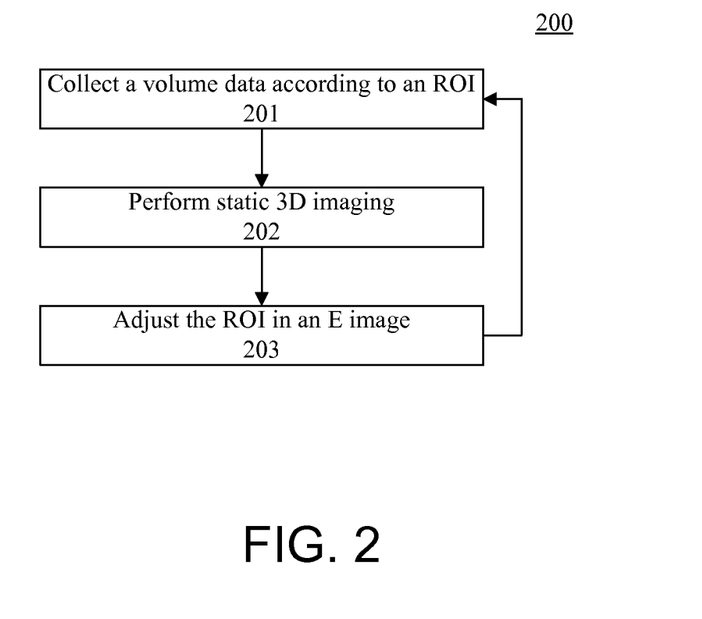
FIG. 2 is a flow chart of a method for ROI adjustment.

In one embodiment, a static 3D image and an E image may be displayed at the same time and may be switched, and a probe needs to swing only once (i.e., just one set of volume data is used for imaging). As shown in FIG. 2, a ROI adjustment method 200 according to this embodiment includes the following steps.

1) Collecting 201 volume data according to an ROI in a 3D/4D imaging mode;

2) Performing 202 static 3D imaging;

3) Adjusting 203 the ROI in an E image by obtaining the E image, selecting the E image, resetting the ROI in the E image, and then re-imaging the ROI reset. The E image may be refreshed in real time.

Figure 3A:
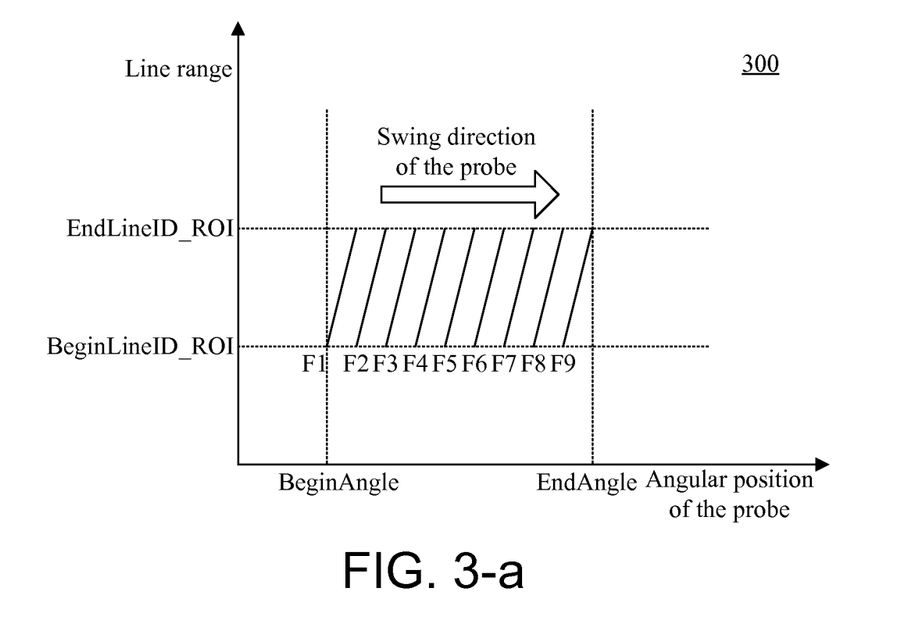

As shown in FIG. 3-a, a scan control mode 300 in imaging may be as follows. In the 3D/4D imaging mode, the system collects volume data according to an ROI; the probe swings from the angular position of BeginAngle to the angular position of EndAngle; the front end of imaging apparatus scans in the manner as shown in FIG. 3-a; and the scan line range and the depth are consistent with those of the ROI selected by the user. The types of images displayed on the screen may include a section image, a 3D image, and an E image. The system may provide for the display of various layouts to the user, and the layouts may include one of the images or any combination of the three images. It should be understood that the frame number in FIG. 3-a is just one example and does not indicate that volume data can only include 9 frames of image data. Instead, the volume data may also include other numbers of frames of image data. The frame number in the following text is also an example, and does not limit the frame number in volume data.

Figure 3B:
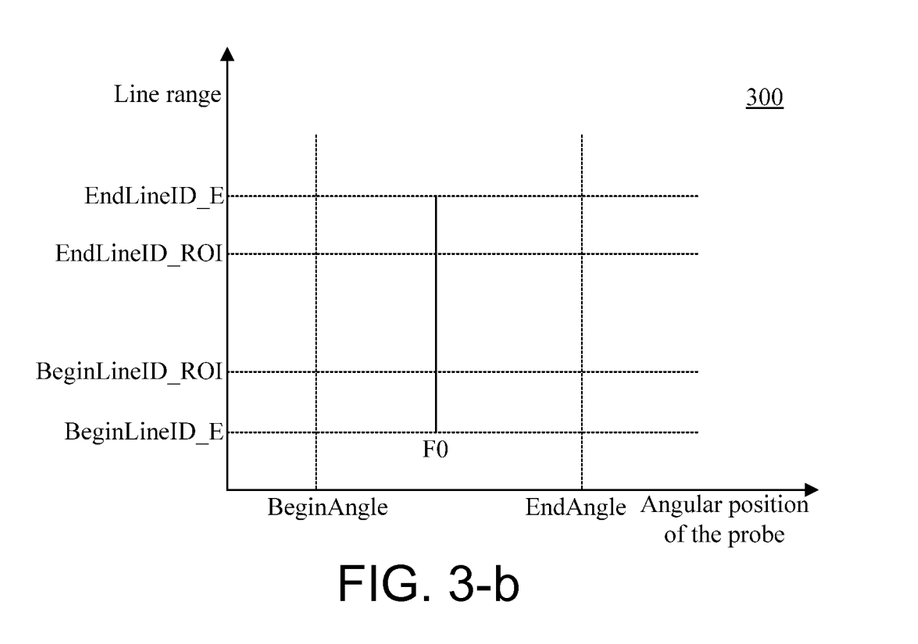

As shown in FIG. 3-b, when the user needs to re-adjust the ROI, the E image is selected, the front end of the imaging apparatus scans in real time in the manner as shown in FIG. 3-b. The probe stops at a certain angular position in the swing angle range. The E image frame is scanned at the angular position and is refreshed in real time (similar to the real-time refresh of the B image, the frame rate is related to sound speed, depth, and scan range). The scan line range [BeginLineID_E, EndLineID_E] and the depth are larger than those of the ROI, so that the user can select a more suitable ROI from the E image. After the user has adjusted the ROI image, the system re-collects volume data according to the new ROI and performs re-imaging.

In another embodiment involving 4D imaging, a 4D image and an E image are displayed at the same time and are refreshed in real time. In the 4D imaging mode, the probe swings back and forth and collects volume data upon swinging in a single direction once to form a 3D image. With a time dimension added, the 3D image is updated in the window in real time to form a 4D image.

Figure 4A:
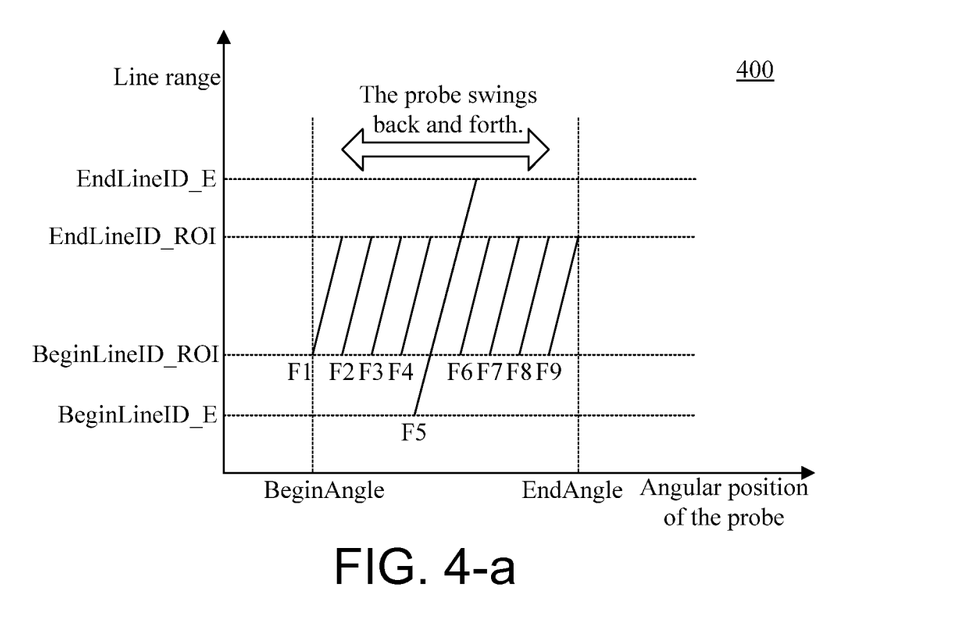

As shown in the scan mode 400 of FIG. 4-a, in this embodiment, the probe swings back and forth, a volume sequence is generated during scanning by the front end of imaging apparatus. The apparatus images the volume sequence and refreshes the image. The types of images that may be displayed on the screen in real time include a section image, a 3D image, and an E image. The apparatus provides for the display of various layouts to the user, and the layouts may include one of the images or any combination of the three images. In order to display the E image, the 4D image, and the section image in real time, each set of volume data scanned by the front end of the imaging apparatus includes common volume data required for imaging, as well as a frame of E image. The front end of the imaging apparatus scanning may be performed in the manner as shown in FIG. 4-a, and during the normal scanning of the ROI scan range, a frame of E image data is scanned. For example, as illustrated, F1, F2, F3, F4, F6, F7, F8, and F9 are common ROI frames, and F5 is an E image frame. The E image is obtained and real-time refreshed through the E image scanning in each volume.

Figure 4B:
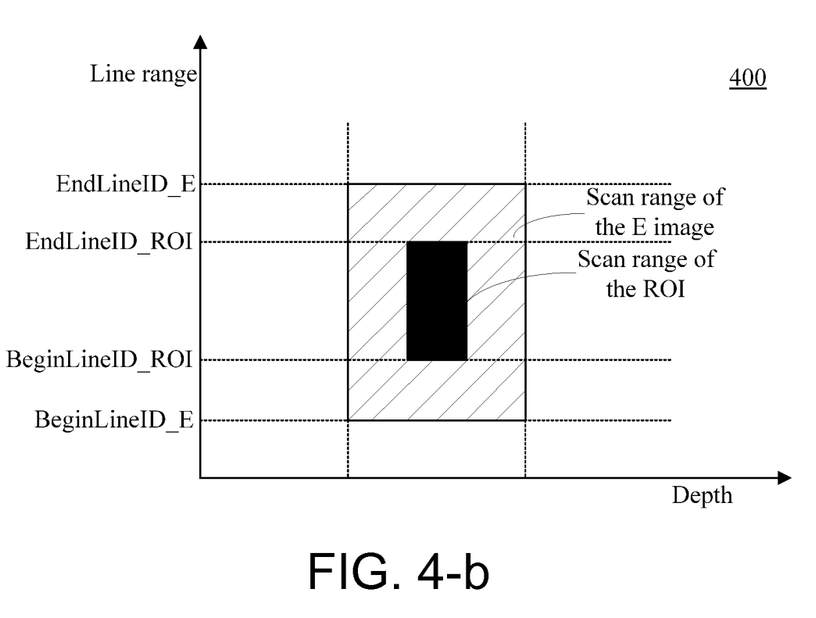

In the scan mode 400 of this embodiment, the scan range of the E image and the scan range of the ROI frame are as shown in FIG. 4-b. The scan range of the E image includes the scan range of the ROI frame, and the scan line range and the scan depth of the E image are both larger than those of the ROI frame. Therefore, in this embodiment, the volume data is formed by F1, F2, F3, F4, F5', F6, F7, F8, and F9, in which F5' is data in the ROI scan range included in the E image frame F5. Such volume data may be used to generate the corresponding section image or 3D image according to display requirements.

Since, in the scan mode of this embodiment, the E image frame and the common volume data are scanned together, the 4D image, the section image, and the E image are all refreshed in real time, and thus the user may select the E image to adjust the ROI in real time when browsing the 4D image.

In another 4D imaging embodiment, the user selects a 4D image or an E image frame for real-time refresh. In the 4D imaging mode, the probe swings back and forth and collects volume data upon swinging in a single direction once to form a 3D image, and with a time dimension added, the 3D image is updated in the window in real time to form a 4D image.

Figure 5:
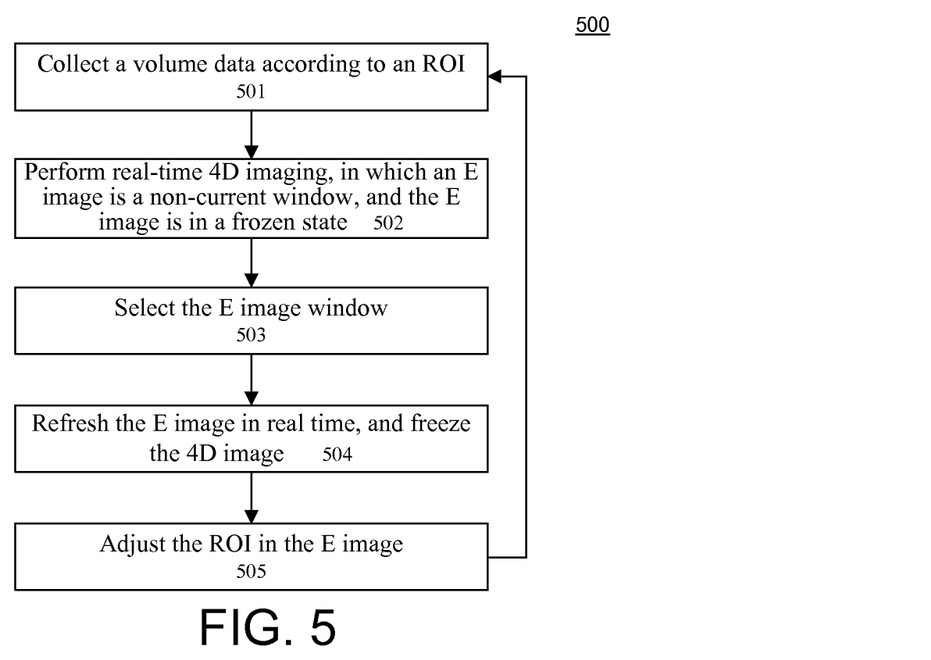
FIG. 5 is a flow chart of a method for ROI adjustment.

As shown in FIG. 5, an ROI adjustment method 500 according to this embodiment may include the following steps.

1) Collecting 501 volume data according to an ROI in a 4D imaging mode.

Figure 6A:
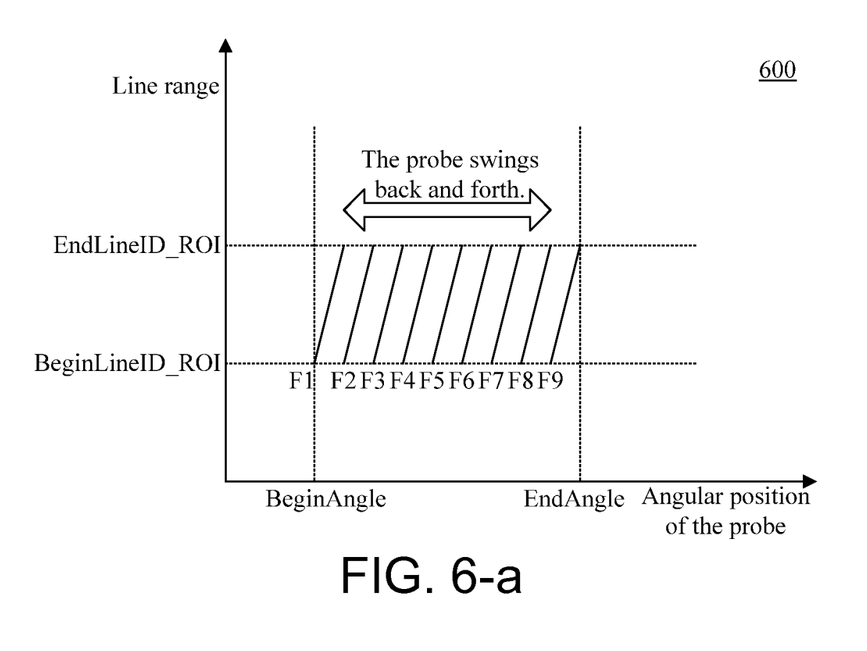

2) Performing 502 real-time 4D imaging. At this time, the scan mode of the front end of the imaging apparatus is as shown in FIG. 6-a, in which the probe swings back and forth and only scans the ROI frame. In a 4D real-time display, an E image is a non-current window, the user may selectively display or not display the E image, and the E image is in a frozen state (not refreshed in real time) when being displayed. In other words, if only imaging is performed, an E image window may not be displayed, or even if the E image window is displayed, the image in the E image window is not refreshed. However, the E image is still in a ready state in the 4D imaging mode at this time, and once the ROI needs to be adjusted, scanning of the E image may be started in the 4D imaging mode at any time.

3) Selecting 503 the E image window when it is needed to adjust the ROI, for example, through triggering by a corresponding functional key set on the volume probe.

Figure 6B:
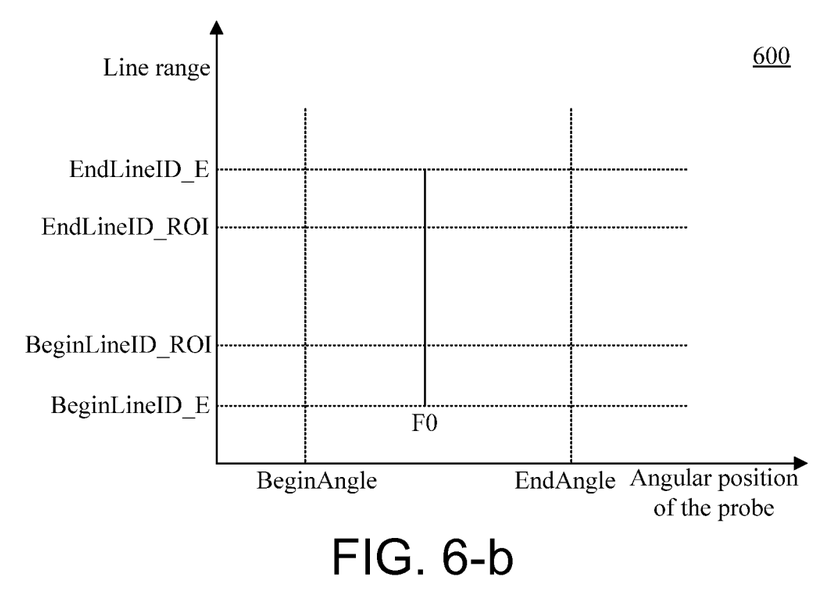

4) Scanning to obtain E image frame. After the E image window is selected, a scan mode 600 of the front end of the imaging apparatus is as shown in FIG. 6-*b*, in which the probe is fixed at a certain angular position in the swing angle range and only scans the E image frame. The scan line range [BeginLineID_E, EndLineID_E] and the depth are larger than those of the common ROI. At this time, the E image is refreshed 504 in real time, and the 4D image is frozen. In the 4D imaging mode, the types of images displayed on the screen may include a section image, a 3D image, and an E image. The system may provide for the display of various layouts to the user, and the layouts may include one of the images or any combination of the three images.

5) Selecting a more suitable ROI from the E image. After the ROI has been adjusted 505, the imaging apparatus re-collects volume data according to the new ROI and performs re-imaging.

In this embodiment, the E image frame and the common ROI frame are scanned at different times, and the frame rate of real-time refresh of the E image frame is higher than that in the second embodiment, which facilitates the user's adjustment of the ROI.

In one embodiment, an ROI adjustment device for 3D/4D imaging is provided, which includes an ROI adjustment module configured to adjust the ROI through an E image in a 3D/4D imaging mode in which the E image may be refreshed in real time and has a scan line range larger than that of the ROI. Such a ROI adjustment device may be implemented in the form of software, such as a computer readable program, or implemented on a hardware platform, such as a field programmable gate array (FPGA), a complex programmable logical device (CPLD), or a digital signal processor (DSP)

A 3D/4D imaging apparatus may also be provided, which includes the above-described ROI adjustment device. The ROI adjustment device may be physically independent, and may be connected to the existing imaging apparatus through an interface so that the existing imaging apparatus has the ROI adjustment function, thus facilitating improvement and upgrading of the existing imaging apparatus. The ROI adjustment device may also be physically integrated into the 3D/4D imaging apparatus, so as to form an integral 3D/4D imaging apparatus having the ROI adjustment function.

In existing systems, ROI adjustment and 3D/4D imaging are two mutually exclusive operations that are respectively performed in a preview mode and an 3D/4D imaging mode. Since switching between the two mode windows is required, the user's operation is complicated. In the methods and apparatuses of this disclosure, the ROI may be directly adjusted in the 3D/4D imaging mode through the E image, so as to avoid the need for exiting the 3D/4D imaging mode and entering the preview mode to adjust the ROI, such that ROI adjustment becomes simple and convenient.

While specific embodiments and applications of various methods and systems have been illustrated and described, it is to be understood that the invention claimed hereinafter is not limited to the precise configuration and components disclosed. Various modifications, changes, and variations apparent to those of skill in the art may be made in the arrangement, operation, and details of the methods and systems disclosed.

Furthermore, the methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified without departing from the scope of the invention as claimed.

The embodiments disclosed may include various steps, which may be embodied in machine-executable instructions to be executed by a general-purpose or special-purpose computer (or other electronic device). Alternatively, the steps may be performed by hardware components that contain specific logic for performing the steps, or by any combination of hardware, software, and/or firmware.

Embodiments of the present invention may also be provided as a computer program product including a non-transitory computer-readable medium having stored thereon instructions that may be used to program a computer (or other electronic device) to perform processes described herein. The computer-readable medium may include, but is not limited to, floppy diskettes, optical disks, CD-ROMs, DVD-ROMs, ROMs, RAMs, EPROMs, EEPROMs, magnetic or optical cards, or other type of media suitable for storing electronic instructions.

Those of skill in the art will appreciate that the various illustrative logical blocks, modules, circuits, and algorithm steps described in connection with the embodiments disclosed herein may be implemented as electronic hardware, computer software, or combinations of both. To illustrate the interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the invention as claimed hereinafter.

What is claimed is:

1. A method for adjusting region of interest (ROI) in three-dimensional/four-dimensional (3D/4D) imaging, comprising:
   obtaining an E image by emitting ultrasonic waves, wherein the E image comprises a reduced data size B-mode image with a reduced data size;
   adjusting, using a processor, a scan line range of the ROI through the E image in a 3D/4D imaging mode, wherein the E image has a scan line range larger than that of the ROI and smaller than or equal to that of a full frame.

2. The method of claim 1, wherein adjusting the ROI through the E image comprises: in static 3D imaging, determining a scan angle, scanning the E image at the position of the scan angle, and adjusting the ROI through the E image.

3. The method of claim 1, wherein adjusting the ROI through the E image comprises: in 4D imaging, scanning a frame of E image in scanning of each set of volume data, and adjusting the ROI through the E image.

4. The method of claim 1, wherein adjusting the ROI through the E image comprises: in 4D imaging, determining a scan angle, scanning the E image at the position of the scan angle, and adjusting the ROI through the E image.

5. The method of claim 1, wherein the E image has a scan depth larger than that of the ROI.

6. The method of claim 1, wherein images displayed in the 3D/4D imaging mode comprise one or more of a 3D/4D image, a section image, and an E image.

7. A device for adjusting a region of interest (ROI) in three-dimensional/four-dimensional (3D/4D) imaging, comprising an ROI adjustment module configured to adjust a scan line range of the ROI through an E image in a 3D/4D imaging mode, wherein the E image has a scan line range larger than that of the ROI and smaller than or equal to that of a full frame.

8. The device of claim 7, wherein the ROI adjustment module adjusts the ROI in the following manner: in static 3D imaging, determining a scan angle, scanning the E image at the position of the scan angle, and adjusting the ROI through the E image.

9. The device of claim 7, wherein the ROI adjustment module adjusts the ROI in the following manner: in 4D imaging, scanning a frame of E image in scanning of each volume data, and adjusting the ROI through the E image.

10. The device according to claim 7, wherein the ROI adjustment module adjusts the ROI in the following manner: in 4D imaging, determining a scan angle, scanning the E image at the position of the scan angle, and adjusting the ROI through the E image.

11. The device of claim 7, wherein the E image has a scan depth larger than that of the ROI.

12. A three-dimensional/four-dimensional (3D/4D) imaging apparatus, comprising a device for adjusting region of interest (ROI) in three-dimensional/four-dimensional (3D/4D) imaging, wherein the device comprises an ROI adjustment module configured to adjust a scan line range of the ROI through an E image in a 3D/4D imaging mode, wherein the E image has a scan line range larger than that of the ROI and smaller than or equal to that of a full frame.

* * * * *